United States Patent
Bruce et al.

(12)

(10) Patent No.: US 6,180,100 B1
(45) Date of Patent: *Jan. 30, 2001

(54) LACTOBACILLUS COMPOSITIONS AND METHODS FOR TREATING URINARY TRACT INFECTIONS

(75) Inventors: Andrew W. Bruce, Toronto; Gregor Reid, London, both of (CA)

(73) Assignee: Urex Biotech., Inc., London (CA)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 09/112,732

(22) Filed: Jul. 9, 1998

Related U.S. Application Data

(62) Division of application No. 08/315,665, filed on Sep. 30, 1994, now Pat. No. 5,804,179.

(51) Int. Cl.$^7$ ............................................. C12N 1/20
(52) U.S. Cl. .............................................. 424/93.45
(58) Field of Search .............................. 424/93.45, 195.1, 424/234.1, 282.1; 435/853–857, 252.9

(56) References Cited

U.S. PATENT DOCUMENTS

| 4,347,240 | * | 8/1982 | Mutai et al. | 424/282.1 |
| 5,372,810 | * | 12/1994 | Onishi et al. | 424/93.4 |

FOREIGN PATENT DOCUMENTS

2397839 * 3/1979 (FR).

OTHER PUBLICATIONS

Newman, The Lancet (Aug. 1915) pp. 331–332.*

Chan et al., Infect. Immun. 47(1): 84–89 (Jan. 1985).*

* cited by examiner

*Primary Examiner*—Jean C. Witz
(74) *Attorney, Agent, or Firm*—Scully, Scott, Murphy & Presser

(57) ABSTRACT

This invention relates to lactobacillus compositions and methods of employing said compositions for treating or preventing urinary tract infections. More particularly, this invention relates to the ability of certain strains of lactobacilli to adhere to uroepithelial or vaginal epithelial cells and to exhibit inhibitory activity against the growth of pathogenic bacteria.

11 Claims, No Drawings

LACTOBACILLUS COMPOSITIONS AND METHODS FOR TREATING URINARY TRACT INFECTIONS

CROSS REFERENCES TO RELATED APPLICATIONS

This is a divisional of U.S. patent application Ser. No. 08/315,665 filed Sep. 30, 1994, now U.S. Pat. No. 5,804,179.

BACKGROUND OF THE INVENTION

This invention relates to bacterial compositions and methods employing said compositions for treating or preventing urinary tract infections. More particularly, this invention relates to the ability of strains of lactobacilli to adhere to uroepithelial or vaginal epithelial cells and associated mucous and to produce an inhibitor against the growth of pathogenic bacteria.

It is well known that indigenous, non-pathogenic bacteria predominate on epithelial cells and associated mucus in the healthy state, and that pathogenic organisms predominate in the stages leading to and during infections. The possibility that indigenous bacteria have a role in preventing infection has been postulated for many years, but few studies have been carried out to identify specific bacteria and their properties required for such an effect.

Urinary tract infections (UTI) are a common cause of illness in both pre- and post-menopausal women. In fact, researchers have estimated that between 10 and 20% of females will develop a UTI during life. In the great majority of these women the infecting organisms originate in the bowel and colonize the perineum, vagina, urethra and bladder in a sequential manner. The majority of infections are caused by *Escherichia coli*. The remaining infections are caused by a variety of bacteria are caused by a variety of bacteria, including *Staphylococcus saprophyticus, Proteus mirabilis,* Klebsiella spp., *Pseudomonas aeruginosa,* enterococci and Staphylococcus For the treatment of many lower urinary tract infections, antibiotic therapy is prescribed. It is recognized, however, that the balance of normal microflora in the urogenital tract, which is disrupted by infection, is further upset by the prolonged use of antimicrobial compounds. (Ohashi H. 1982 *Kansenshogaku Zasshi,* 56:647–654). Accordingly an alternate treatment for urinary tract infections is desirable.

U.S. Pat. No. 4,314,995 to Hata et al. investigated anaerobic, lactobacilli-like organisms as a means of treating a number of infectious diseases, but no consideration was given to the combined importance of bacterial adherence, competitive exclusion and inhibitor activity, and no discussion was included of the treatment of urinary tract infections.

U.S. Pat. No. 4,347,240 to Mutai et al. discloses a composition and method employing a specific strain of lactobacilli to inhibit tumor growth.

SUMMARY OF THE INVENTION

The present invention provides a method for the treatment or prevention of urinary tract infections of mammals including humans which comprises administering a safe and effective amount of one or more lactobacillus viable whole cells, non-viable whole cells, cell wall fragments or inhibitory substances. The lactobacillus is of one or more species of lactobacillus which adheres to uroepithelial or vaginal epithelial cells.

The preferred strains of lactobacilli within the scope of this invention are aerobic and microaerophilic isolates which particularly after growth in urine and in brain heart infusion yeast extract medium:

a) adhere to uroepithelial or vaginal epithelial cells, b) competitively exclude pathogenic bacteria from adhering to uroepithelial or vaginal epithelial cells, c) produce an inhibitor activity against the growth of pathogenic bacteria.

Also defined within the present invention are compositions suitable for treating or preventing urinary tract infections of mammals including humans which comprise one or more lactobacillus viable whole cells, non-viable whole cells, cell wall fragments or inhibitory substances and a pharmaceutically acceptable carrier, wherein the lactobacillus is of one or more species of lactobacillus which adheres to uroepithelial or vaginal epithelial cells.

PREFERRED EMBODIMENTS

In a preferred aspect, the lactobacillus is aerobically or microaerophilically grown and may be selected from the group consisting of *Lactobacillus casei, L. acidophilus, L. plantarum, L. fermentum, L. brevis, L. jensenii* and *L. crispatus.*

More specifically, the lactobacillus may be aerobically grown and is selected from the group consisting of *Lactobacillus casei* var *rhamnosus* GR-1 (ATCC. 55826), *L. casei* var *rhamnosus* GR-2 (ATCC. 55915) *L. casei* var *rhamnosus* GR-3 (ATCC. 55917), *L. casei* var *rhamnosus* GR-4 (ATCC. 55916), *L. casei* var *rhamnosus* RC-9, *L. casei* var *rhamnosus* RC-17 (ATCC. 55825), *L. casei* var *alactosus* RC-21, *L. casei* NRC 430 and *L. casei* ATCC 7469.

Alternatively, the lactobacillus may be microaerophilically grown and selected from the group consisting of *L. rhamnosus* RC-12(ATCC 55895), *L. acidophilus* RC-25, *L. plantarum* RC-19, *L. jensenii* RC-11 (ATCC. 55920), *L. acidophilus* ATCC 4357, *L. plantarum* ATCC 8014, *L. fermentum* A-60, and *L. fermentum* B-54 (ATCC. 55884).

In a preferred form of the present invention, the lactobacillus is selected to be substantially resistant to spermicide. Details are provided hereinbelow.

In another aspect of this invention, a pharmaceutical composition is provided for treating or preventing urinary tract infections in humans and lower animals which comprises a safe and effective amount of one or more of the said aforementioned lactobacilli, cell wall fragments or inhibitory substances with a pharmaceutically acceptable carrier.

Although this invention is not intended to be limited to any particular mode of application, intravaginal, intraurethral or periurethral installation of the compositions are preferred. The compositions may be installed in the form of a cream, liquid, paste, gel or suppository as desired. One preferred form is a cream formulation comprising one or more lactobacillus viable whole cells, non-viable whole cells, cell wall fragments or inhibitory substances in a jelly base, preferably a K-jelly base. Another preferred form of application involves the preparation of a freeze-dried capsule comprising the composition of the present invention. It has been found that a capsule comprising $10^9$ organisms is suitable.

By "safe and effective amount" as used herein is meant an amount of lactobacillus high enough to significantly-positively modify the condition to be treated but low enough to avoid serious side effects (at a reasonable benefit/risk ratio), within the scope of sound medical judgment. A safe and effective amount of lactobacillus will vary with the particular condition being treated, the age and physical condition of the patient being treated, the severity of the condition, the duration of treatment, the nature of concurrent therapy, and the specific lactobacillus employed. We have found that at least 10 lactobacilli, and preferably 20 to 30, and more preferably more than 40 said bacteria adhered to epithelial cells are desired. The effective amount of lactobacillus will thus be the minimum amount which will provide the desired attachment to epithelial cells. The presence of $5 \times 10^9$ bacteria, as viable or non-viable whole cells, in 0.05 ml. solution of phosphate buffered saline solution, or in 0.05 ml. of suspension of agar, or the dry weight equivalent of cell wall fragments, has been found effective when administered in quantities of from about 0.05 ml. to about 20 ml.

By "pharmaceutically-acceptable carrier" as used herein is meant one or more compatible solid or liquid filler diluents, or encapsulating substances. By "compatible" as used herein is meant that the components of the composition are capable of being comingled without interacting in a manner which would substantially decrease the pharmaceutical efficacy of the total composition under ordinary use situations.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations. Wetting agents and lubricants such as sodium lauryl sulfate, as well as colouring agents, flavouring agents, lubricants, excipients, tabletting agents, stabilizers, anti-oxidants and preservatives, can also be present.

Lactobacilli have been found to bind to urinary mucus, a property associated with colonization of uroepithelial surfaces (Reid and Sobel, 1987. *Reviews of Infectious Diseases* 9:470–487).

It has been found that one group of patients at risk of acquiring an infection are those requiring long term and intermittant catheterization. Catheter insertion causes trauma and acts as a focus for pathogenic bacteria to colonize the uroepithelium and the catheter itself in dense microcolonies which are resistant to antibiotic penetration. This leads to persistant infection. By utilizing the adherence capacity of lactobacilli, it is possible to coat the uroepithelium and catheter surfaces thereby excluding pathogens from colonizing and causing an infection. The use of inhibitory substances produced by lactobacilli will also protect the host from colonization of both uroepithelium and catheter surfaces by the pathogenic organisms.

Accordingly, in a further aspect of this invention, a novel method of treating or preventing urinary tract infections is provided which involves coating a biologically compatible prosthetic device with a safe and effective amount of one or more of lactobacillus viable whole cells, non-viable whole cells, cell wall fragments or inhibitory substances and inserting the device into the urogenital tract.

The biologically compatible prosthetic device may be composed of polymers such as fluorinated ethylene propylene, sulfonated polystyrene, polystyrene, or polyethylene terephthalate and in addition, glass. The device may be a catheter such as a urinary or peritoneal catheter, an IUD or other intravaginal, intrauterine, or intraurethral device.

Very successful coverage of such devices with the lactobacillus of the present invention has been achieved.

Accordingly, in a preferred form of treatment of urinary tract infections or the prevention of urinary tract infections, the patient is administered a safe and effective amount of a lactobacillus composition in accordance with the present invention, for example, periurethrally, and is then installed with a prosthetic device pre-coated with the lactobacillus viable whole cells, non-viable whole cells, cell wall fragments or inhibitory substances of the present invention. Alternatively, the prosthetic device may not be pre-coated but may be inserted into a patient having been administered a, for example, periurethral pre-coat of the lactobacillus composition described above. With the administration of the composition prior to prosthetic device insertion, an indigenous protective flora is formed which may effectively compete with uropathogens emerging as a result of antibiotic selection or other natural events.

Although the normal microbial flora of the vagina in the maintenance of a healthy state is not completely understood, it is believed that Lactobacillus species play a part in the protection against colonization by pathogenic microorganisms. It has been found that women with a history of urinary tract infections have a urogenital flora dominated by pathogens whereas lactobacilli predominate in healthy women. The ecological balance of the vagina can be upset in a number of ways, including the prolonged use of antibiotics and pregnancy. In addition, researchers have implicated the diaphragm as a predisposing factor in recurrent urinary tract infections (Fihn S D, Latham R H, Roberts P, Running K, Stamm W E 1985 Association between diaphragm use and urinary tract infection *J. Am. Med. Assoc.* 254: 240–245). A number of studies have found that women using this form of contraception are between 1.5 and 4.1 times more likely to develop urinary tract infection. It has been suggested that increased pressure of the diaphragm on the female urethra may be in part responsible for this. However, the diaphragm is usually used in conjunction with a spermicidal cream or foam and these preparations have been found to have a bactericidal effect on some protective bacteria such as lactobacillus. In addition, it has been found that some uropathogens, such as Candida sp. grow and survive in spermicides. It has now been established by the applicant that certain lactobacilli which are, as discussed above, beneficial or protective bacteria, are spermicide resistant and can therefore be administered to female mammals who may be using or want to use a spermicide preparation, in order to treat or prevent urinary tract infections. By using the spermicide resistant strains of lactobacilli, the beneficial effect of treating urinary tract infections is not diminished or negated in situations requiring the intravaginal insertion of a spermicidal preparation.

A most preferred composition comprises one or more lactobacillus viable whole cells which are selected tor-be substantially spermicide resistant, a spermicide and a pharmaceutically acceptable carrier. This composition may be administered intravaginally or intraurethrally in the form of a cream, capsule, gel, paste or suppository. Alternatively, but equally effectively, the lactobacillus composition may be administered in a separate preparation from the spermicide, for example, after spermicide insertion.

Preferably, the lactobacillus is selected from the group comprising *L. casei* ss *rhamnosus*, *L. casei* ss *alactosus*, *L.*

*fermentum* and *L. brevis*. Most preferably, the lactobacillus is either *L. casei* var *rhamnosus* GR-1 or *L. fermentum* B-54. Preferably, they are resistant to greater than 25% concentration of spermicide. The list provided herein is not intended to be exhaustive. A skilled technician with the present disclosure could readily determine other suitable substantially spermicide resistant lactobacilli.

Preferably, the spermicide is of the nonoxynol group, most preferably, nonoxynol-9. Other spermicides are acceptable as long as the administered lactobacilli are substantially resistant to these selected spermicides.

Not only would female mammals:

1) in need of a treatment for urinary tract infection; and 2) requiring the use of a spermicide preparation benefit from this method and composition, but also female mammals not immediately in need of such treatment but who can be considered "prone" to urinary tract infections and who also require the use of a spermicide preparation. These individuals can benefit by treatment with both the spermicide resistant lactobacillus and the spermicide either separately or in one convenient preparation.

The ability of lactobacillus to exclude uropathogens from the urinary tract likely involves and is influenced by numerous factors and effects including:

1) the adherence of lactobacillus to uroepithelial or vaginal epithelial cells, and 2) the size of the lactobacillus. (Reid et al. 1987, *Journal of Urology* 138:330–335, the contents of which are incorporated herein by reference).

Although the present invention is not bound by any one theory or mode of operation, it is believed that, at least to some degree, a combination of coaggregation of lactobacillus with uropathogens and the production by lactobacillus of one or more inhibitory substances may be responsible for excluding pathogens and/or reducing their numbers in the urinary tract.

From the standpoint of physical exclusion, the attachment of lactobacillus acts as a block to uropathogens by preventing access to receptor sites. Although complete exclusion of uropathogens theoretically can occur, the most common finding of the results of the present invention is that there is a reduction in uropathogen numbers compared to lactobacilli. In other words, although some lactobacilli may not completely exclude uropathogens, they are still capable of interfering with uropathogen colonization in vivo. Coaggregation is an important element as it allows lactobacilli to form a urogenital mixed flora present in healthy patients. This mixed flora is preferably dominated by lactobacilli and other indigenous gram positive bacteria. It is hypothesized that the lactobacilli of the present invention and some uropathogens coaggregate (Reid et al. 1988, *Can. J. Microbiol.* 34:344–351, the entire contents of which are incorporated herein by reference), in a way that interferes with the pathogenic process.

In one embodiment of the present invention, it may not necessary to use lactobacillus viable whole cells, non-viable whole cells or cell wall fragments. It has been found that lactobacillus exhibits an inhibitory activity on uropathogens which does not appear to be solely cell-associated. The factor or factors which are responsible shall be referred to as the inhibitory substance(s).

This inhibitory substance(s) may be readily separated from cultured lactobacillus cells by techniques such as filtration, precipitation and centrifugation which are readily known and applied in the art. The preferred techniques for the selection of the inhibitory substance(s) will be readily apparent to a skilled artisan from the detailed examples provided hereinbelow.

It is believed that the inhibitory substance or substances are metabolic by-products such as hydrogen peroxide or acids (lactic) and bacteriocin-like compounds which are peptide or protein in nature. The activity of this inhibitory substance or substances does not disappear upon dialysis against PBS indicating that the substance probably has a molecular weight greater than 12,000–14,000. In addition, the bioactivity of the inhibitory substance produced by at least some of the lactobacilli of the present invention was retained under pH buffered conditions, was bacteriocidal, and was heat labile.

A number of assays were devised to examine the ability of lactobacilli to adhere to epithelial cells, to competitively exclude pathogenic bacteria from adhering to epithelial cells, and to produce an inhibitor activity against the growth of pathogenic bacteria.

The invention will now be illustrated by means of the following non-limiting examples.

EXAMPLE 1

Different growth media were tested to determine their effect on adherence of lactobacilli to squamous and transitional epithelial cells. The organisms were grown aerobically overnight at 37° C., then harvested and incubated with the epithelial cells, obtained from the urine of healthy women, and the adherence of the lactobacilli was assayed by a technique described in Reid et al., *Journal of Infectious Diseases*, September 1983.

Table 1 shows adherence to epithelial cells of *L. casei* strain GR-1 grown in different culture media. This study established that aerobically grown lactobacilli attached in large numbers to epithelial cells, and that the organisms grew well in human urine, which is important for use of lactobacilli for treatment or prevention of urinary tract infections.

TABLE 1

| Growth media | Lactobacilli per epithelial cell |
|---|---|
| BYE Broth | 62.68 |
| BYE Tween | 48.83 |
| MRS Broth | 48.40 |
| BHI Broth | 49.28 |
| TS Broth | 51.85 |
| Urine | 73.00 |
| BYE Agar | 63.78 |
| BYE Tween | 52.60 |
| MRS Agar | 48.13 |
| BHI Agar | 50.68 |
| TS Agar | 60.73 |
| Rogosa's Agar | 38.08 |

BYE = brain heart infusion medium (BBL Microbiology Systems, Becton Dickinson & Co. Cockeysville, U.S.A.). with 0.5% yeast extract; Tween = 0.1% Tween 80, (BBL, USA); MRS = Lactobacillus MRS medium (Difco USA); BHI = brain heart infusion medium (BBL, USA); TS = trypticase soy (BBL, USA); Rogosa's = Rogosa SL, lactobacilli selective medium (Difco, USA).

BYE=brain heart infusion medium (BBL Microbiology Systems, Becton Dickinson & Co. Cockeysville, U.S.A.). with 0.5% yeast extract; Tween=0.1% Tween 80, (BBL, USA); MRS=Lactobacillus MRS medium (Difco USA); BHI=brain heart infusion medium (BBL, USA); TS=trypticase soy (BBL, USA); Rogosa's=Rogosa SL, lactobacilli selective medium (Difco, USA).

EXAMPLE 2

In order to correlate the in vitro and in vivo results, further studies were completed.

*L. casei* strains GR-1 and RG-17 and *L. acidophilus* were grown in brain heart infusion yeast extract media, human urine and human urine with 0.5% glucose and 0.5% lactose and were found to produce exopolysaccharide material and to attach well to uroepithelial cells in vitro (Cook et al. 1988, *Current Microbiology* 17:159–166). Endocervical, vaginal and periurethral epithelial cells from normal healthy premenopausal women also showed the presence of encapsulated lactobacillus attached to the cells. These results correlate the in vivo and in vitro data.

EXAMPLE 3

Different stages of the lactobacillus cell cycle were examined and adherence was found to occur best in the stationary phase of growth (Cook et al. *Cur. Microbiol.*). Capsule production was found in vitro and has also been noted in vivo (Reid et al. 1989).

Further studies with strains *L. casei* GR-1, douche and RC-17, *L. acidophilus* 76, and T-13 and *L. fermentum* A-60 were conducted and it was found that bacterial surface hydrophobicity and charge can alter with growth conditions. However, the bacteria were still able to attach to uroepithelial cells even with altered hydrophobic and charge properties.

There is a correlation between the receptivity of uroepithelial cells for bacteria/bacterial adherence to the cells in the in vivo and in vitro environment. Specifically, it has been found that lactobacillus adhesion to uroepithelial cells can a reflection of the in vivo adhesion of lactobacillus to the cells (Reid, 1988. *Current Microbiology* 18: 1989, pp. 93–97), although precise numbers may vary between patients.

Accordingly, the in vitro results presented herein are considered a reliable indication of the corresponding in vivo situation.

EXAMPLE 4

Lactobacilli strains were isolated from the urethra, cervix and vagina of healthy women with no history of urogenital tract infections. The strains were identified as lactobacilli and speciated by methods described in the Virginia Polytechnic Institute (VPI) Laboratory Manual (*Anaerobe Laboratory Manual,* 4th edition, 1977, published by VPI Anaerobe Laboratory, Blacksburg, Va.). The adherence of aerobic and microaerophilic strains to epithelial cells was tested using an in vitro assay which employed uroepithelial cells from urine sediment. It should be noted that the adherence values vary depending upon the receptivity of the host cells. The menstrual cycle affects this receptivity, and maximum adherence occurs prior to ovulation and prior to menstruation. (Chan et al., *Journal of Urology*, March 1984). The uroepithelial cells used in the experiments of Table 2 were harvested from women on the tenth day of their menstrual cycle, to optimise subsequent attachment of lactobacilli.

The results shown in Table 2 establish the high adherence capacity of aerobic and microaerophilic lactobacilli.

TABLE 2

| Strains | Lactobacilli attached per epithelial cell |
|---|---|
| *L. casei* GR-1 | 44.50 |
| *L. casei* GR-2 | 51.83 |
| *L. casei* GR-3 | 33.85 |
| *L. casei* GR-4 | 37.93 |
| *L. casei* RC-9 | 17.80 |
| *L. casei* RC-17 | 118.70 |
| *L. casei* RC-21 | 27.83 |
| *L. rhamnosus* RC12 | 17.43* |
| *L. plantarum* RC-19 | 23.28* |
| *L. acidophilus* RC-25 | 14.88* |
| *L. jensenii* RC-11 | 31.50* |
| *L. casei* NRC 430 | 30.35 |
| *L. casei* ATCC 7469 | 35.68 |
| *L. acidophilus* ATCC 4357 | 19.43* |
| *L. plantarum* ATCC 8014 | 18.23* |
| *L. acidophilus* T-13 | 14.00* |
| *L. fermentum* A-60 | 52.15 |
| *L. fermentum* B-54 | 39.00 |

The lactobacilli were grown aerobically except where signified "*", which identifies organisms grown microaerophilically in 10% $Co_2$, as this condition was found to improve the bacterial attachment of these particular lactobacilli strains. Comparative studies have shown that the aerobic strains tend to grow more rapidly and attach to epithelial cells in larger numbers than microaerophilic strains. The ability of lactobacilli to grow rapidly in aerobic and microaerophilic conditions, particularly in urine medium, provides the organisms with an opportunity to attach to and colonize epithelial cells and associated mucus in the urinary tract, enhancing their competition with pathogenic bacteria, which are known to grow rapidly under similar conditions.

It is preferred that lactobacilli adhere to epithelial cells in at least greater than 10 bacteria per cell, more preferably greater than 25 and more preferably still greater than 40 bacteria per cell, using the adherence assay described by Reid et al., (1983) and using epithelial cells harvested at peak times of receptivity, as defined by Chan et al., (1984), both referred to above.

EXAMPLE 5

The following studies were designed to test specific lactobacillus isolates for their ability to competitively exclude common pathogenic bacteria from adhering to epithelial cells. An in vitro assay was designed which involved incubating lactobacilli with uroepithelial cells for 30 minutes at 37° prior to incubation with the radiolabelled pathogens for 30 minutes at 37° C., as described by Chan et al., *Infection and Immunity*, January 1985. The percentage inhibition caused by lactobacilli was measured from the numbers of radiolabelled organisms adhering to epithelial cells in test and control samples, as shown in Table 3.

The results demonstrate the ability of lactobacilli to competitively block pathogenic bacteria from adhering to epithelial cells, which demonstrates that lactobacillus strains can be used to prevent urinary tract-infections. Studies have shown that *L. casei* GR-1 can detach uropathogens from uroepithelial cells (up to 45% detachment) supporting the use of lactobacilli in treating infections. This detachment is very important as it means that lactobacilli given to prone patients can remove uropathogens, adhere themselves, coaggregate and form a protective balance in the urogenital tract.

TABLE 3

| Lactobacillus | Pathogenic Bacteria | | | | | |
|---|---|---|---|---|---|---|
| | 1 | 2 | 3 | 4 | 5 | 6 |
| | % Inhibition of attachment of pathogens | | | | | |
| L. casei GR-1 | 94 | 100 | 86 | 74 | 61 | 71 |
| L. casei GR-2 | 84 | 81 | 100 | 58 | 59 | 79 |
| L. casei GR-3 | 50 | 46 | 100 | 83 | 37 | 77 |
| L. casei RC-9 | 57 | 28 | NT | NT | 69 | NT |
| L. casei RC-21 | NT | 100 | NT | NT | 14 | NT |
| L. casei ATCC 7469 | 42 | 58 | 53 | 30 | 66 | 75 |
| L. plantarum ATCC 8014 | 51 | 82 | 76 | 71 | 44 | 75 |
| L. fermentum A-60 | 51 | 37 | 100 | 82 | 30 | 65 |
| L. acidophilus T-13 | 42 | 0 | 21 | 74 | 0 | 63 |
| L. fermentum B-54 | 39 | 0 | 53 | 50 | 0 | 64 |

1 = E. coli strain C1212-77; 2 = E. coli mannose sensitive strain; 3 = Proteus mirabilis strain 28cii; 4 = Klebsiella pneumoniae strain 3a; 5 = Pseudomonas aeruginosa mucoid; 6 = Pseudomonas aeruginosa non-mucoid; NT = not tested.

1=E. coli strain C1212-77; 2=E. coli mannose sensitive strain; 3=Proteus mirabilis strain 28cii; 4=Klebsiella pneumoniae strain 3a; 5=Pseudomonas aeruginosa mucoid; 6=Pseudomonas aeruginosa non-mucoid; NT=not tested.

EXAMPLE 6

It is clear from Table 3 that although some lactobacilli did not completely exclude uropathogens, they are still responsible for the interference of uropathogen colonization in vivo. It has been found that this is-due to many factors and may involve coaggregation between the lactobacillus and the uropathogens.

A coaggregation assay was designed, based in part upon the method of Cisar, 1982 (Coaggregation Reactions Between Oral Bacteria: Studies of Specific Cell-to-Cell Adherence Mediated by Microbial Lectins. In, Host-Parasite Interactions in *Periodontal Diseases,* eds. R. J. Genco and S. E. Mergenhagen, pp.121–131, ASM Publications, Washington, D.C.). To each well of a microtray was added 500 microliters each of lactobacilli (human distal urethral isolate, *L. casei rhamnosus* GR-1, GR-2, RC-17, RC-9, *L. acidophilus* 76 (ATCC 4357), *L. fermentum* A-60, *L. casei* douche, *L. brevis* 189, and *L. acidophilus* T-13) and the selected uropathogen (*Escherichia coli* strain Hu 734, strain ATCC 25922, *E. coli* 2239 or *E. coli* 917). After mixing, the trays were incubated at 37° C. at 100 rpm for 4 hours, then the suspensions were scored for coaggregation. The scoring system of 0 for no coaggregation to 4 for marked coaggregation was developed in line with the system described by Cisar. To develop a satisfactory reproduceable assay for coaggregation, standard buffers were used.

The results, which indicated that lactobacillus can coaggregate with *E. coli* and other uropathogens, has a bearing upon the importance of lactobacillus in vivo, particularly if inhibitor production accompanies coaggregation. These results also imply that the phenomena of coaggregation is of real clinical importance in the interaction of microorganisms in the urogenital tract.

The ability of lactobacilli to bind to uropathogens did not appear to be restricted to one species or a single strain, with all nine strains demonstrating coaggregation with two or more uropathogens (Reid et al., *Can. J. Microbiol.* 34:344–351 1988) the entire contents of which is incorporated herein by reference).

In a further series of in vitro studies, the following results were obtained:

TABLE 4

Combinations of urogenital flora found to coaggregate in vitro

| COAGGREGATING PAIRS | | SCORE* |
|---|---|---|
| L. casei GR-1 | with S. epidermidis 1938 | 2 |
| | with E. coli 2239 | 2 |
| | with streptococcus 6698 | 1 |
| | with enterococcus 6696 | 1 |
| | with enterococcus 1331 | 1 |
| | with diphtheroid II | 1 |
| L. acidophilus 76 | with E. coli 2239 | 1 |
| L. brevis 189 | with E. coli 2239 | 1 |
| L. fermentum A-60 | with E. coli 2239 | 4 |
| Diphtheroid II | with enterococcus 1331 | 2 |
| | with streptococcus 6696 | 4 |
| Streptococcus 6698 | with E. coli 2239 | 1 |
| Enterococcus 1331 | with E. coli 2239 | 2 |
| S. saprophyticus YA | with L. acidophilus T-13 | 1 |

*Scores from/0 = no coaggregation to maximum of 4.

In order to assess the nature and extent of coaggregation in vivo, introital, vaginal and endocervical specimens were collected at regular intervals from the introitus, vaginal wall and cervix of 25 healthy, pre-menopausal women at regular intervals during the menstrual cycle, both before and after a vaginal wash. The bacteria in these samples were identified by standard microbiological methods.

The coaggregation assay was performed using the technique described hereinabove.

The in vivo results seem to indicate that coaggregation of lactobacillus with potential uropathogens (gram-positive cocci and gram-negative rods) can result in a balanced ecological niche and a healthy status for the patient. Therefore, complete exclusion of uropathogens may not be necessary for protection from infection. This likely depends upon numerous factors, including host effects, as well as bacterial growth parameters and inhibitor production by specific lactobacillus strains.

The ability of strains of normal flora, isolated by micromanipulation, to reaggregate in vitro further supports the observations of coaggregate formation in vivo.

EXAMPLE 7

Data has been obtained demonstrating that lactobacilli adherence to epithelial cells is important in the exclusion of uropathogenic bacteria. Experiments determined that non-viable whole cells and cell wall fragments of lactobacilli attached to epithelial cells, and excluded the attachment of uropathogenic bacteria. These experiments have been carried out using a strain of lactobacilli now identified as *L. casei* GR-1, grown aerobically in urine. The lactobacilli preparations were first incubated with the uroepithelial cells from the urine sediment for 30 minutes at 37° C. prior to incubation with the radiolabelled uropathogenic bacteria (*E. coli, K. pneumoniae. P. aeruginosa*) for 30 minutes at 37° C., as disclosed in Chan et al *Infection and Immunity,* January 1985. The results demonstrated that formalin-killed whole cells gave 38 to 72% blockage of uropathogenic bacterial adherence (Mean=46%), acid-treated whole cells gave 5 to 31% blockage (Mean=20%), and other cell wall fragments gave a range of from 4 to 75% blockage (Mean=34%). The cell wall fragments included lipoteichoic acids, peptidoglycan, and fragments obtained by sonication, sodium dodecyl sulfate (SDS) extraction and SDS extraction with acid treatment. The lactobacilli preparations prevented the pathogenic organisms from adhering to the epithelial cells by a steric hindrance effect and blocking the receptor sites access normally used by the pathogenic bacteria. The results obtained using the lactobacilli whole cell and cell wall fragment preparations show that non-viable lactobacilli preparations attach to epithelial cells and can be used to exclude pathogenic bacteria from adhering to the cells.

EXAMPLE 8

Studies have shown that uroepithelial cells from patients with a urinary tract infection are colonized with pathogenic bacteria (mean of 20 bacteria per cell in a study of 37 patients). The administration of antibiotics often eradicates these organisms, unless they are encased in a microbial biofilm. However, the bacteria-free uroepithelial cells are still receptive to bacterial adherence, as indicated in Table 5, where *E. coli* strain C1212-77 was incubated with uroepithelial cells in vitro from women on antibiotic therapy, and assayed using the method of Reid et al., (1983), referred to above. The high attachment figures illustrate that the patients are still receptive to recolonization, and that other protective measures are required to exclude the uropathogens. (Reid et al. 1988)

TABLE 5

| | *E. coli* attached per epithelial cell |
|---|---|
| Patient 1 | 76.90 |
| Patient 2 | 77.68 |
| Patient 3 | 52.30 |
| Patient 4 | 71.60 |
| Patient 5 | 122.70 |
| Patient 6 | 82.85 |
| Patient 7 | 58.45 |
| Patient 8 | 51.53 |
| Patient 9 | 119.35 |
| Patient 10 | 36.70 |
| Patient 11 | 36.55 |

Similar high attachment figures were obtained for other uropathogens, including other *E. coli* strains, *Proteus mirabilis*, *Klebsiella pneumoniae* and *Pseudomonas aeruginosa*. Seven of these 11 patients developed a recurrent UTI within the months following this study indicating their continued susceptibility.

Based upon the data which show that lactobacilli whole cells and cell wall fragments competitively excluded pathogenic bacteria from adhering to epithelial cells, precolonization of the epithelial cells from patients (such as those 11 shown in Table 5) with lactobacilli would have acted as a protective barrier against attachment with uropathogens.

Colonization of the epithelial cells and associated mucus with lactobacilli preparations can be used to prevent UTI from recurring. In the case of the 11 patients in the study shown in Table 5, such treatment would be expected to have prevented UTI from recurring in 7 patients.

EXAMPLE 9

In addition to adhering to epithelial cells and preventing the colonization with pathogenic bacteria, lactobacilli possess other properties which prevent pathogens from colonizing epithelial surfaces. Lactobacilli strains which adhered to epithelial cells were tested for an inhibitory activity, using an agar overlay technique similar to the technique disclosed in *Performance Standards for Anti-Microbial Discs Susceptibility Tests* published by The National Committee for Clinical Laboratory Standards (1979), modified in-that the bottom layer contained lactobacilli, the top layer was spread with *E. coli*, and antibiotic discs were not applied. One ml of $10^9$ lactobacilli per ml was inoculated into the bottom layer of agar; the top layer was added; the plates were incubated at 37° C. overnight, then the pathogenic bacteria ($10^9$ per ml) were streaked onto the top layer, and the plates incubated at 37° C. overnight.

The growth of lactobacilli on the bottom layer of agar was found to inhibit growth of pathogenic bacteria on the top layer. The results presented in Table 6 illustrate that this inhibitory activity is an important factor in combination with bacterial adherence to enable lactobacilli to be used as an agent to treat or prevent infection.

TABLE 6

| | 1 | 2 | 3 | 4 | 5 | 6 | 7 | 8 | 9 | 10 |
|---|---|---|---|---|---|---|---|---|---|---|
| *L. casei* GR1 | + + | + + | + + | – – | + + | + + | + + | + – | + + | + – |
| *L. casei* GR2 | + – | + – | + + | – – | – – | + + | + + | – – | + + | + – |
| *L. casei* GR3 | + – | + + | + – | – – | + + | + + | + + | + – | – – | + – |
| *L. casei* GR4 | + + | + + | + + | + – | + + | + + | + + | + – | + + | + – |
| *L. casei* RC9 | + – | + + | + + | + – | + + | + + | + + | + – | + + | + – |
| *L. casei* RC17 | + – | + – | + + | – – | – – | + – | + + | + + | + + | + – |
| *L. casei* RC21 | + – | + – | + + | – – | – – | + + | + + | + – | + + | + – |
| *L. rhamnosus* RC12 | + – | + – | + – | – – | + + | + + | + + | + – | + + | + – |
| *L. plantarum* RC19 | + – | + – | + – | – – | – – | + – | + – | NT | NT | NT |
| *L. acidophilus* RC25 | – – | + – | + – | – – | – – | + – | + – | NT | NT | NT |
| *L. jensenii* RC11 | + – | + – | + – | + + | – – | + + | – – | NT | NT | NT |
| *L. casei* NRC 430 | + – | + – | + – | + – | + – | + + | + + | + – | + + | + – |
| *L. casei* ATCC 7469 | + – | + + | + + | + – | + + | + + | + + | – – | + – | + – |
| *L. acidophilus* ATCC 4357 | + + | + + | + + | + – | + + | + + | + + | + + | + + | + – |
| *L. plantarum* ATCC 8014 | + – | + – | + – | – – | + + | + + | + + | + + | + + | + – |
| *L. fermentum* A60 | – – | – – | – – | – – | – – | – – | – – | – – | + + | – – |

+ + = complete inhibition, + – = partial inhibition, – – = no inhibition; NT = not tested
1 = *E. coli* C1212-77; 2 = *E. coli* C1214-77; 3 = *E. coli* Hu 734; 4 = *K. pneumoniae* 3a; 5 = *P. mirabilis* 28 cii; 6 = *Pseudomonas aeruginosa* non-mucoid; 7 = *Pseudomonas aeruginosa* mucoid; 8 = *Staphylococcus saprophyticus* YA; 9 = enterococci 1331; 10 = *Staphylococcus aureus* 1750.

EXAMPLE 10

Strains of lactobacilli were isolated from the urogenital tract of pre-menopausal women in accordance with the methods outlined in the Virginia Polytechnic Institute, *Anaerobic Laboratory Manual*, Blacksburg, Va. Uropathogens were isolated from women with urinary tract infections that represented the bacteria associated most commonly with urinary tract infections. The strains expressed adhesons that have been reported to be important in uropathogenic colonization of the uroepithelium, namely mannose sensitive and mannose resistant adhesons and the presence of a capsule. The uropathogens included *E. coli* strains C1212-77, Hu734, C1214-77, *Klebsiella Pneumoniae* 3a, *Staph. aureus* 1750 and enterococcus 1331.

An agar overlay assay was developed for this experiment. The lactobacilli were added to molten brain heart infusion yeast extract agar, poured into a petri dish, and allowed to set. A second suspension of uninnoculated agar was poured over the first layer and the plate was incubated at 37° C. overnight in a humidified 10% carbon dioxide atmosphere. The uropathogens were then innoculated onto the top layer and the plate was re-incubated overnight. The inhibition of growth of the uropathogens was expressed as complete inhibition, partial inhibition and no inhibition.

A partial summary of the results obtained are presented hereinbelow:

TABLE 7

The Inhibition of Growth of 10 Uropathogens by Lactobacilli

| Lacto-bacilli | E. coli | | | | P. Mirabilis |
|---|---|---|---|---|---|
| Strain | C1212 | C1214 | 734 | 67 | 28cii |
| GR-2 | Partial | Partial | Complete | No | No |
| GR-1 | Complete | Complete | Complete | No | Complete |
| GR-4 | Complete | Complete | Complete | Partial | Complete |
| GR-3 | Partial | Complete | Partial | Complete | Complete |
| 558 | Partial | Complete | Complete | No | Complete |
| 81 | Partial | Partial | Partial | No | Partial |
| RC-15 | No | No | No | No | No |
| RC-21 | Partial | Partial | Complete | No | No |
| RC-9 | Partial | Complete | Complete | Partial | Complete |
| RC-16 | Partial | Partial | No | No | No |
| RC-26 | Complete | Partial | No | No | No |
| 76 | Complete | Complete | Complete | Complete | Complete |
| RC-10 | No | No | No | Partial | No |

| Lacto-bacilli | P. aeuroginosa | | Staph. saprophy- | Entero-coccus | Staph. aureus |
|---|---|---|---|---|---|
| Strain | P(S) | P(R) | ticus YA | 1331 | 1750 |
| GR-2 | Complete | Complete | No | Complete | Partial |
| GR-1 | Complete | Complete | Partial | Complete | Partial |
| GR-4 | Complete | Complete | Partial | Complete | Partial |
| GR-3 | Complete | Complete | Partial | No | Partial |
| 558 | Complete | Complete | No | Partial | Partial |
| 81 | Complete | Complete | Partial | Partial | Complete |
| RC-15 | No | No | No | No | No |
| RC-21 | Complete | Complete | Partial | Complete | Partial |
| RC-9 | Complete | Complete | Partial | Complete | Partial |
| RC-16 | No | Partial | No | No | Partial |
| RC-26 | Partial | Partial | No | No | Partial |
| 76 | Complete | Complete | Partial | Complete | Complete |
| RC-10 | No | No | Partial | Partial | Complete |

*L. acidophilus* 76 had the highest score of inhibitory activity of the human isolates, *L. casei* GR-4 and RC-9 showed inhibitory activity against all uropathogens.

The results verify that lactobacilli exhibits inhibitory activity against uropathogens. The inhibitory substances, as described herein, diffuse through the agar which indicates that they are not cell associated, although this does not totally rule out that some cell associated inhibition is present (Reid et al., 1987 *The Journal of Urology* 138:330–335 the entire contents of which are incorporated herein by reference).

EXAMPLE 11

The activity of the inhibitory substance produced by lactobacillus was studied in two phases in Reid et al. *Can. J. Microbiol.* 34:334–351.

The first phase involved a sandwich plate technique. A 1 ml suspension of lactobacilli (*L. casei* ssp. *rhamnosus* GR-1) was added to 9 ml molten BYE agar, poured onto a plate, allowed to set, and covered with an overlay of 10 ml BYE agar. Following 24 hours incubation at 37° C., the indicator bacteria (*E. coli* Hu 734 or ATCC strain 25922) were innoculated onto the surface of the plate. Following a further 24-hour incubation, the inhibition of growth of the indicator bacteria was scored as complete inhibition (++), partial inhibition (+-), or no inhibition (--).

Various conditions were then tested for the expression of inhibitory activity including varying the concentration of the lactobacillus inoculum on the underlay, changing the conditions from aerobic to microaerophilic to anaerobic and varying the incubation temperature by heating the underlay to 80° C. for 2 hours prior to innoculating with the indicator strain.

The results of the first phase indicate that *L. casei* GR-1 produces substances inhibitory to uropathogenic bacteria. The inhibition was evident following growth of a small inoculum of *L. casei* GR-1 prior to innoculation of the indicator bacteria, suggesting that a metabolic product of *L. casei* was responsible for bioactivity. The acidic inhibitory effect on the sandwich plates was found to be heat stable and inhibitory to *E. coli*.

The second phase was undertaken to optimize the inhibitory effect and to determine whether it was solely due to a pH effect. For these studies, the effect of acid and pH were assessed by using nutrient agar as the underlay, resulting in a pH at 6.7 following lactobacillus growth. In addition, a 24-hour MRS culture filtrate of *L. casei* GR-1 neutralized with sodium hydroxide was assayed for activity against the uropathogens using a disc diffusion assay.

The results of the second phase indicate that there was an effect additional to acid. This inhibitory activity of *L. casei* GR-1 was still present in agar buffered to maintain a final pH of 6.7 as well as in filtrates neutralized with sodium hydroxide. These findings indicate that the inhibitory activity is separate from an acid or pH effect. This was later found to be a heat labile specific inhibitor.

The results of phases I and II are presented below in Table 8:

TABLE 8

Properties Associated with the Inhibitor Produced by *L. casei* GR-1

| Phase 1 | Inhibitory activity not neutralized for acid<br>Requires inoculum of >$10^5$ bacteria on sandwich plate<br>Activity produced after 4 h growth in air, in $CO_2$, and aerobically<br>The acidic activity on the sandwich plates was heat stable<br>Activity not due to bacteriophages or hydrogen peroxide |
|---|---|
| Phase 2 | Inhibitory activity neutralizing acid<br>Optimum production from MRS cultures<br>Activity present in MRS filtrate neutralized with NaOH |

The inhibitory activity including the effects of acid was heat stable; however, the actual inhibitory substance(s) of the present invention is heat labile and, due to its production under anaerobic conditions, distinct from solely acid and hydrogen peroxide.

EXAMPLE 12

Concentrations of up to 80% ammonium sulphate were added to *L. casei* GR-1 culture filtrates treated with chloroform vapours and centrifuged at 15,000× g for 15 minutes. The supernatants and pellets were dialysed against two changes of PBS over a period of 24 hours and tested for inhibitory activity by a disc diffusion assay.

Chloroform, hexane, ether, propanol, and acetonitrile were each combined with an equal volume of sterile, filtered MRS-GR-1 supernatant, shaken, and allowed to separate. The solvents and water soluble phases were then tested for bioactivity against *E. coli* Hu 734 and ATCC 25922 by a disc diffusion assay. Controls were included to rule out the possibility of solvent residue affecting viability of the *E. coli* indicator bacteria.

The results indicated that even after treatment with up to 80% ammonium sulphate, bioactivity of GR-1 remained within the supernatant material and was not precipitated with the salt. The activity was not lost upon dialysis of the supernatant against buffer.

In addition, of the solvents tested, the chloroform extract of GR-1 supernatant alone appeared to possess inhibitory activity. The ability to inhibit *E. coli* transferred from the MRS broth supernatant to the chloroform extract. The inhibitory activity of MRS broth supernatants extracted with propanol, hexane, acetonitrile or ether remained in the aqueous phase. Controls of solvent alone did not inhibit the *E. coli*.

Both *L. casei* GR-1 and *L. acidophilus* 76 were found to possess some antimicrobial activity against *E. coli*. Due to the copious quantities of extracellular polysaccharides produced by L. acidophilus 76, GR-1 is considered to be the superior isolate.

The attempts to precipitate the active components of the GR-1-MRS filtrates with up to 80% ammonium sulphate were unsuccessful, as the bioactivity remained within the supernatant. However, it was found that activity did not disappear upon dialysis against PBS, indicating that the substance probably has a molecular weight greater than 12,000–14,000, and is, therefore, neither lactic acid nor hydrogen peroxide.

In an attempt to further isolate and purify the inhibitory compound(s), the GR-1-MRS culture filtrate was subjected to extraction with a range of solvents. The bioactivity detectable with the disc diffusion assay was found to be soluble in chloroform.

EXAMPLE 13

Various lactobacilli were isolated from chicken and from the human female urogenital tract and were cultured on MRS agar or broth (Difco, Detroit). Twenty presumptive strains of enterococci were isolated from female patients with urinary tract infections. The enterococci were stored at 70° C. in brain heart infusion broth supplemented with 2% yeast extract (Difco, Detroit), termed BYE, plus 20% glycerol.

Ten microliters of an 18-hour stationary culture of the enterococci were streaked down the centre of a BYE plate and spread evenly over the surface with a sterile swab. Five microliters of the lactobacilli cultures or culture filtrates (passed through a 0.22 micrometer filter) being tested were applied to 6 ml diameter filter paper discs, and transferred onto the surface of agar plates seeded with enterococci. The plates were incubated at 4° C. for 3 hours to allow diffusion of the cultures, followed by 18 hours at 37° C. before being examined for zones of inhibitions surrounding the discs.

The lactobacilli were examined for the ability to inhibit each other's growth by the disc diffusion assay as described above, substituting lactobacilli swabbed onto MRS agar plates for enterococci on BYE agar plates.

It was found that *L. casei* RC-15, *L. rhamnosus* RC-6, *L. jensenii* RC-28 and *L. fermentum* B-54 (ATCC. 55884) produced 2 ml clear zones surrounding the filter paper discs and accordingly were found to have inhibitory activity towards enterococci.

This activity was not due to acid or low pH, nor was it due to a bacteriocin, and indications are that these strains produce protein or peptide substances similar to that produced by GR-1 but with a 'different antibacterial spectrum (McGroarty and Reid, 1988, *Microbiol Ecology in Health and Disease*, in press).

EXAMPLE 14

The development of urinary tract infections is primarily caused by organisms colonizing the intestine, then sequentially colonizing the perineum, vaginal introitus, urethra and bladder. This is referred to as an ascending infection. In some patients, the infection ascends further into the ureters and kidneys to give rise to pyelonephritis. There is no ideal animal model which can be used to study the ascending infections of humans. Therefore, the two animal systems described herein were used to examine the ability of lactobacilli to prevent pathogenic bacteria from colonizing the epithelium of the bladder and kidneys. However, the bladder cells comprise transitional and squamous epithelial cells, the latter type being similar to those of the perineum, vaginal introitus and urethra. Therefore, the results from the animal experiments may also be used to demonstrate that the lactobacilli will competitively exclude uropathogens from colonizing epithelial cells of the type found in the perineum, vaginal introitus, urethra, bladder, ureters and kidneys. The results obtained from the animal experiments (Examples 14 and 15) support the use of lactobacilli preparations to prevent infections of the urinary tract.

Female Sprague Dawley rats were used as a model for chronic UTI. A transurethral instillation of uropathogenic bacteria, incorporated into an agar bead suspension, were injected into the bladder. This resulted in long term colonization of the uroepithelium of the bladder (up to log 7.3 viable bacteria after 2 months) and kidneys up to log 8.9 bacteria after 2 months (as discussed in Reid et al., *Infection and Immunity*, August 1985, incorporated herein by reference). However, by instilling lacobacilli 3 weeks prior to challenge, the uropathogens were not found to attach and multiply, and UTI was prevented in 84% of animals (21 protected out of 25 tested). Furthermore, although the lactobacilli attached to and colonized the uroepithelium, there was no adverse response detected in the hosts against these non-pathogenic bacteria.

EXAMPLE 15

The second model was that of an acute UTI, using CBA mice. A similar protocol was followed to that described for Example 14, except that lactobacilli incorporation of $5\times10^9$ bacteria in 0.05 ml. solution of phosphate buffered saline, and also the equivalent in agar beads, was tested. The lactobacilli were instilled 2 days prior to challenge, and the animals sacrificed after 24 shours. The results demonstrated that 19 of 30 mice did not develop infection after treatment with lactobacilli in a phosphate buffered saline suspension, whereas 28 of 30 control mice developed UTI. The animals given lactobacilli incorporated into agar beads also showed a degree of protection (67% protected). The strain of lactobacilli- used in the mouse and rat model experiments was *L. casei* var rhamnosus GR-1.

Only 2% of mice treated with strain *L. casei* GR-1 and possessing greater than $10^3$ lactobacilli in the bladder and only 8% with greater than $10^4$ lactobacilli in the kidney were infected with *E. coli* (Reid et al. 1989. In, *Host-Parasite Interactions in Urinary Tract Infections*, University of Chicaco Press). This demonstrates a high level of protection against infection even within these invasive surfaces.

The fact that other strains of lactobacilli have been found to attach to epithelial cells and have also been found to produce inhibitory activity against the growth of pathogenic bacteria demonstrates that adherent lactobacilli strains producing an inhibitor activity will be effective in competitively excluding pathogenic bacteria from the epithelial mucosa, and thus be effective for treating or preventing urinary tract infections.

EXAMPLE 16

Human volunteers, both male and female, aged 43 to 76 years with at least one year of symptomatic recurrent bacteriuria, were implanted with *L. casei* GR-1 into the urinary bladder to determine whether the bacteria infected the patients and to assess whether bladder colonization could be achieved.

The results demonstrated that these bacteria did not infect the patients and bladder colonization was not the preferred route to colonize and prevent recurrent urinary tract infections (Hagberg et al. 1988, In, *Host-Parasite Interactions in Urinary Tract Infections*, University of Chicago Press).

Further studies were then undertaken based on intravaginal and perineal instillation of lactobacilli into human female patients suffering from recurrent urinary tract infection (UTI). (Bruce and Reid *Can. J. Microbiol.* 34: 339–343 1988).

*L. casei* ssp. *rhamnosus* GR-1 cells were grown in MRS broth (Difco, Detroit) for 24 h at 37° C., harvested, and resuspended in physiological saline to a concentration of $10^{11}$ organisms/mL. Twice weekly, each of the patients instilled 1 mL of this viable bacterial solution deeply into the vagina and swabbed their introitus and perineum with a similar preparation. After instillation, in the adult patients a tampon was inserted into the vagina to prevent leakage overnight, with a view to maximizing colonization with lactobacilli. The lactobacilli preparations were found to maintain viability in solution at 4° C. for up to 5 weeks. This proved useful in achieving patient compliance, and reduced the number of required visits.

Urine specimens, and vaginal and perineal swabs were obtained at regular intervals to test for the presence of bacteria. The urine was cultured by the Microbiology Department at Toronto General Hospital using standard techniques. Vaginal and perineal specimens were also cultured for the presence of aerobic coliforms, gram-positive cocci, diphtheroids, yeasts, and lactobacilli. The cultures were not quantitated, although the most dominant organism present was noted.

To assess whether lactobacilli colonized the vaginal epithelium, specimens were obtained prior to commencement of the study and subsequent to lactobacilli instillation. Vaginal epithelial cells were harvested, washed in phosphate-buffered saline (PBS,pH7.1), and stained with Gram's stain, and 50 cells were evaluated under light microscopy for the numbers of lactobacilli (gram-positive rods) adherent.

A 38-year-old control subject who had no history of UTI was treated with a single intravaginal instillation of *L. casei* GR-1 and monitored for lactobacilli colonization over a 5-week period. At the time of instillation, she was colonized by a lactobacilli strain (not identified), which had distinctly different colonial morphology than GR-1.

All the patients had full urologic work-up and had no congenital abnormalities, no reflux, and no neurogenic disease. The urines were sterile in each case, prior to commencement of the trial.

(Patient P.E.)

This 56-year-old woman presented with persistent lower urinary tract irritative symptoms with documented *E. coli* bacteriuria during antibiotic (nitrofurantoin low dose therapy, 50 mg/day) treatment and in between full dose treatment episodes. She was on Premarin, an estrogen supplement. Her urinary tract symptoms always followed sexual intercourse. Pretherapy vaginal and perineal cultures showed the presence primarily of coliform bacteria, and secondary colonization with streptococci, staphylococci, and diphtheroids. No lactobacilli were detected upon culture or examination of her vaginal epithelial cells. The irritative symptoms were present prior to instillation of lactobacilli.

The lactobacilli were successfully instilled, with a colonization level of 37 lactobacilli per vaginal epithelial cell (see Table 8). She tolerated the treatment, with no side effects, and reported an improvement in well-being, gain in weight, less tiredness, and no problems following sexual intercourse. Her irritative symptoms disappeared for the most part over a 6-month period and she remained infection free for 6 months.

(Patient K.R.)

This 28-year-old woman had a past history of repeated coliform UTIs during and after her first pregnancy, 18 months prior to entering the trial. She suffered from persistent infection during long-term antibiotic therapy and between episodes of short-term treatment. She wished to become pregnant and felt that lactobacilli therapy provided a suitable alternative to antibiotic medication. No lactobacilli were detected upon vaginal and perineal culture, although she was colonized with gram-positive cocci and coliforms. Following instillation of *L. casei* GR-1, she became well colonized with the lactobacilli (60 bacteria per vaginal epithelial cell). She tolerated the treatments well and reported no adverse side effects. Although gram-positive cocci were present in vaginal and perineal cultures during lactobacilli therapy, no coliforms were isolated from her urogenital tract and the patient remained infection free for 4 months. Treatment was-discontinued and in a 5-month follow-up, she remained infection free.

(Patient O.H.)

This is a 52-year-old woman with a history of persistent irritative symptoms and UTI (confirmed by monthly cultures), including breakthrough infections while on various antibiotics. She was not receiving any estrogen therapy. No lactobacilli were isolated from her vagina and perineum, but gram-positive cocci and coliforms were isolated. She became well colonized upon instillation of L. casei GR-1 (67 bacteria per vaginal epithelial cell). Her treatment was well tolerated, with no side effects and no irritative symptoms. Following treatment, no infection or symptoms ensued for 3–5 months.

(Patient T.S.)

The only child entered in this study was a 13- year-old girl who had a history of on average 20 documented lower UTIs per year since the age of 4. The infections were not related to sexual abuse, hygiene, bath irritants, or urinary tract abnormalities. Previous long- and short-term treatments with antibiotics had limited success and did not prevent recurrent coliform infections. Prior to lactobacilli instillation, her urogenital tract showed the presence of lactobacilli which did not inhibit her coliforms in vitro, but she was predominantly colonized with E. coli, as well as enterococci, coagulase-negative staphylococci, diphtheroids, and additional gram-positive cocci. She tolerated the lactobacilli instillations well and her mother noted a refreshingly healthy change in her appearance and attitude. The GR-1 colonized the vagina (110 bacteria/cell) and no coliforms were detected over a 6-week period. Due to an episode of gastroenteritis, not related to lactobacillus therapy, her treatment was discontinued.

(Patient L.P.)

The fifth patient was a 32-year-old mother of two with a 2-year history of irritative symptoms and persistent UTI, documented by cultures, and found to be mainly due to coliform bacteria. A strain of lactobacillus was isolated from her vagina, prior to therapy, and this had colony morphology distinct from L. casei GR-1 and showed no inhibitory activity in vitro against coliforms or enterococci. She tolerated the lactobacilli therapy and reported no adverse effects. The lactobacilli attached poorly to her vaginal epithelial cells (4 bacteria/cell) but existed as the dominant organism in the vagina for 4 weeks as found from the culture results. The vagina was consistently colonized also with enterococci, and these organisms caused a breakthrough symptomatic UTI which required antibiotics to eradicate. The patient re-entered the study with another 4-week infection-free period, but this was followed by another enterococcal infection. In an attempt to challenge the enterococci, a combination of L. casei GR-1 and L. acidophilus 76 (a high acid producing lactobacilli strain) was given. The lactobacilli colonization increased to 11 bacteria per vaginal epithelial cell and the patient became infection free for a further 4 weeks.

(Control)

The lactobacilli colonized the vagina of the healthy control subject for up to 5 weeks after a single instillation. The patient's own lactobacillus strain also remained, but was not found to predominate.

The results are tabulated hereinbelow:

TABLE 8

Results of clinical study where L. casei GR-1 was instilled twice weekly into the vagina and onto the perineum of five females who had a history of persistent UTI

| Patient | Age (years) | Outcome | Level of lactobacilli colonization achieved* |
| --- | --- | --- | --- |
| P. E. | 56 | 6 months infection free | 27 |
| K. R. | 28 | 4 months infection free | 60 |
| O. H. | 52 | 3.5 months infection free | 67 |
| T. S. | 13 | 6 weeks infection free | 110 |
| L. P. | 32 | 4 weeks infection free (twice) 4 weeks infection free on L. casei GR-1 and L. acidophilus 76 | 4 |

*Data are given as mean number of bacteria per vaginal cell.

The results of this study are encouraging in that all five of the patients benefited from the therapy, by having an improved well-being and by remaining free of UTI for period of time longer than that obtained with other therapeutic modalities. L. casei GR-1 colonized the vagina and perineum of each patient and did not itself cause any urogenital infection. The levels of lactobacilli colonization varied for each patient, as determined by evaluating adherence to vaginal epithelial cells.

Of the five patients receiving therapy, all showed protection from UTI, especially in three cases where this time span was reasonably lengthy (3.5 to 6 months). None of the patients reported any side effects to the treatment. It was felt that the present technique of treatment was not invasive and was seen to be simply restoring a normal indigenous flora to the urogenital tract.

In general, the therapeutic approach of the clinical trial received the approval of the five patients, although there were some reservations regarding the use of a fluid and the insertion of a tampon. The use of lactobacilli was preferred by all the patients to antibiotic treatment, and could be particularly useful for prevention of UTI in pregnant women. It is noteworthy that patient K.R. was protected by lactobacilli therapy for 4 months, and has remained colonized by lactobacilli and infection free for an additional 5 months, supporting the concept that restoration of the normal flora can be beneficial in preventing recurrent urinary tract infections.

EXAMPLE 17

The women in the studies described in Example 16 indicated a preference for a cream or a suppository over a liquid and tampon-based formulation. Accordingly, a full-scale clinical trial is underway using a suppository formulation.

Preliminary data on 3 patients indicates that a cream formulation comprising L. casei GR-1, L. fermentum B-54 in a K-jelly base is one effective combination treatment to prevent the onset of UTI following intravaginal and peri-urethral installation once weekly. The cream consists of $3 \times 10^{11}$ L. casei GR-1, $3 \times 10^{10}$ L. fermentum B-54 made up to a total of 3 ml bacteria added to 27 grams of K-jelly base. No adverse side effects have been incurred in any of the human experiments and, in fact, each patient has emphasized an improved benefit to her health when on the treatment.

The effectiveness of using suppositories in a skim milk base has also been noted, particularly in colonizing the vagina and preventing urinary infections.

EXAMPLE 18

The following study was undertaken to show the in vivo and in vitro colonization of prosthetic devices by lactobacilli.

Polyethylene intrauterine devices (IUDs) were aseptically removed from 6 sexually active, asymptomatic, pre-menopausal women (aged 18–35). These devices had been in place for 2 years. Lactobacilli were found attached to the IUDs as determined by culture, fluorescent antibody and acridine orange staining techniques. This indicates that:

1) biofilms of indigenous bacteria can occur on prosthetic devices without inducing a symptomatic infection,
2) the lactobacilli colonize the prosthetic device and remain viable over a period of time.

Polyethylene IUDs and silkolatex urinary catheters (sectioned into small strips of approximately 2 cm in length) were then used for in vitro adhesion studies.

The prosthetic devices were placed in 15 ml MRS broth (Difco, Detroit) containing 1% bacterial inoculum of *L. casei* GR-1, GR-2 and RC-17, *L. fermentum* A-60, and *L. acidophilus* T-13. Following 24 to 48 hours incubation at 37° C., 100 rpm, the cultures were fixed and appropriately stained.

These organisms were found to adhere to IUDs and urinary catheters within 24 hours.

Additional experiments verified that lactobacilli adhered to polyethylene terephthalate, polystyrene, and sulphonated polystyrene and to silkolatex catheter material. Accordingly, lactobacilli have been found to bind to various surfaces in vivo and in vitro (Reid et al. 1988, *Microb. Ecol.* 16:241–251, the entire contents of which are incorporated herein by reference).

Further experiments demonstrated that lactobacilli could coat urinary catheters to the extent of 94% coverage (as measured by image analysis) within 9 hours. In addition, the adhesion of lactobacilli to polymers significantly reduced the adhesion of uropathogens, further supporting the use of lactobacilli as anti-infection agents.

With the accumulated data and results presented herein from human trials in the bladder and vagina, it is evident that lactobacilli can be used to protect a catheterized patient from the onset of UTI.

EXAMPLE 19

Nonoxynol-9 (N-9) is a membrane-active detergent and the active ingredient of many spermicidal creams and foams. It is incorporated in these preparations at 5% and 12.5% (wt/wt) respectively. It immobilizes sperm by disrupting the cell membrane and acts similarly on bacteria and viruses. The effect of N-9 on the growth of lactobacilli has been examined, in vitro.

Vaginal swabs were obtained from 44 premenopausal women with and without vaginitis, who used a variety of birth control methods. Smears from the swabs were Gram stained, examined for the presence of lactobacilli, and plated onto lactobacilli MRS agar (MRS) and brain-heart infusion agar supplemented with 2% yeast extract (BYE agar). The plates were incubated at 37° C. for 18 h in 5% $CO_2$. Organisms recovered from the plates were identified as lactobacilli with the API rapid CH kit and stored at −70° C. in MRS broth plus 20% (wt/vol) glycerol. Freeze-dried lactobacillus isolates from the laboratory collection originally isolated from chicken, dairy and human sources were also cultured on MRS agar and broth.

Doubling dilutions of N-9 (Ortho Pharm., Canada) were made in MRS (pH 6.5) and BYE broth (pH 7.4) ranging from 0.1% to 25% (wt/vol). The pH of the N-9-supplemented medium was adjusted to the same level as unsupplemented medium where necessary. Lactobacillus isolates were subcultured three times prior to testing in the N-9 broths. The cultures were washed three times in phosphate-buffered saline, pH 7.1 (PBS), and resuspended to a concentration of $10^7$ cells $mL^{-1}$. Aliquots of 50 uL were added to test tubes in triplicate containing 3 mL of either medium alone or medium plus N-9, mixed thoroughly, and incubated for 18 h at 37° C. The tubes were scored for growth, and the M.I.C. was recorded as the lowest concentration demonstrating no growth. Aliquots of 50 uL were transferred from N-9/MRS tubes showing no growth to 3 mL of fresh MRS, incubated for 18 h at 37° C., and examined for turbidity.

TABLE 9

Minimum inhibitory concentration of N-9 for lactobacilli

| Lactobacillus species | Number of strains | Minimum inhibitory concentration | |
|---|---|---|---|
| | | <1.0% | >25.0% |
| Lactobacillus spp.[a] | 18 | 12 (67%) | 6 (33%) |
| L. acidophilus | 12 | 8 (67%) | 4 (33%) |
| L. plantarum | 2 | 1 (50%) | 1 (50%) |
| L. casei ss rhamnosus* | 8 | 1 (13%) | 7* (88%) |
| L. casei ss alactosus | 1 | 0 (0%) | 1 (100%) |
| L. jensenii | 3 | 3 (100%) | 0 (0%) |
| L. fermentum** | 2 | 1 (50%) | 1** (50%) |
| L. brevis | 1 | 0 (0%) | 1 (100%) |

[a]Fresh vaginal isolates, not speciated.
*includes GR-1
**includes B-54

TABLE 10

Lactobacillus sensitivity to N-9: relationship to source of organisms

| Source of lactobacilli | Number of isolates | Sensitive[a] | Resistant[b] |
|---|---|---|---|
| Vagina[c] | 18 | 12 (67%) | 6 (33%) |
| Urogenital tract[d] | 25 | 12 (48%) | 13 (52%) |
| Dairy | 1 | 0 (0%) | 1 (100%) |
| Chicken | 3 | 2 (67%) | 1 (33%) |
| Total | 47 | 26 (55%) | 21 (45%) |

[a]N-9 MIC <1%
[b]N-9 MIC >25%
[c]Fresh clinical isolates
[d]Stored laboratory strains Nonoxynol-9 minimum inhibitory concentrations for a total of 47 lactobacilli sources are shown in Table 9 above. Fifty-five percent (26/47) of the strains were inhibited by 0.1% to 1.0% of N-9 and 45% (21/47) were able to grow in the presence of 25% of N-9, the maximum concentration tested. Of the 26 strains that showed suppression of growth in concentrations of N-9 less than 1.0%, 15 were rendered non-viable in concentrations of N-9 less than or equal to 1.0%. The-growth of the remaining 11 strains was simply suppressed in the presence of N-9. There was no correlation between particular species or the source of the bacteria and the N-9 susceptibility of the lactobacilli (refer to Table 10 above).

Accordingly, the fresh vaginal isolates of lactobacillus-could be split into two groups according to their nonoxynol-9 minimum inhibitory concentrations: 67% (12/18) had minimum inhibitory concentrations for N-9 between 0.1% and 1.0%. The remainder grew in 25%, twice the maximum concentration used for contraceptive purposes. This latter group of lactobacilli were termed resistant.

Given the above selection procedure, it would be fairly routine to determine which strains of lactobacilli are spermicide resistant and accordingly, which strains could be used within the scope of the preferred embodiment of the present invention.

The following microorganisms were deposited with the American Type Culture Collection, 12301 Parklawn Drive, Rockville, Md. 20852: *Lactobacillus casei* var *rhamnosus* GR-1, ATCC 55826 on Oct. 3, 1996; *Lactobacillus rhamnosus* GR-2, ATCC 55915 on Dec. 19, 1996; *Lactobacillus rhamnosus* GR-3, ATCC 55917 on Dec. 19, 1996; *Lactobacillus rhamnosus* GR-4, ATCC 55916 on Dec. 19, 1996; *Lactobacillus jensenii* RC-28, ATCC 55918 on Dec. 19, 1996; *Lactobacillus rhamnosus* RC-6, ATCC 55894 on Dec. 10, 1996; *Lactobacillus rhamnosus* RC-12, ATCC 55895 on Dec. 10, 1996; *Lactobacillus rhamnosus* A-60, ATCC 55896 on Dec. 10, 1996; *Lactobacillus jensenii* RC-11, ATCC 55920 on Dec. 26, 1996; *L. casei* var *rhamnosus* RC-17, ATCC 55825 on Oct. 3, 1996; and *Lactobacillus fermentum* B-54, ATCC 55884 on Nov. 26, 1996.

What is claimed is:

1. A method for restoring normal indigenous flora to a mammalian urogenital tract which comprises administering a therapeutically effective amount of at least one Lactobacillus strain selected from the group consisting of *L. casei* var. *rhamnosus* GR-1, *L. casei* var. *rhamnosus* GR-2, *L. casei* var. *rhamnosus* GR-3, *L. casei* var. *rhamnosus* GR-4, *L. casei* var. *rhamnosus* RC-17, *L. casei* ATCC-7469, *L. rhamnosus* RC-12, *L. acidophilus* RC-25, *L. jensenii* RC-11, *L. acidophilus* ATCC-4357, *L. plantarum* ATCC 8014, *L. fermentum* A-60 and *L. fermentum* B-54.

2. A pharmaceutical composition effective to restore normal indigenous urogenital flora in a mammal which comprises an effective amount of at least one Lactobacillus strain selected from the group consisting of *L. casei* var. *rhamnosus* GR-1, *L. casei* var. *rhamnosus* GR-2, *L. casei* var. *rhamnosus* GR-3, *L. casei* var. *rhamnosus* GR-4, *L. casei* var. *rhamnosus* RC-17, *L. casei* NRC-430, *L. casei* ATCC-7469, *L. rhamnosus* RC-12, *L. acidophilus* RC-25, *L. jensenii* RC-11, *L. acidophilus* ATCC-4357, *L. plantarum* ATCC 8014, *L. fermentum* A-60 and *L. fermentum* B-54 wherein the lactobacillus strain is administered in unit dosage form comprising at least $10^9$ organisms.

3. The composition of claim 2 in the form of a capsule or tablet.

4. The composition of claim 3 wherein said capsule comprises $10^9$ organisms.

5. A method for colonizing a urogenital tract in a mammal which comprises administering a therapeutically effective amount of at least one Lactobacillus strain selected from the group consisting of *L. casei* var. *rhamnosus* GR-1, *L. casei* var. *rhamnosus* GR-2, *L. casei* var. *rhamnosus* GR-3, *L. casei* var. *rhamnosus* GR-4, *L. casei* var. *rhamnosus* RC-17, *L. casei* ATCC-7469, *L. rhamnosus* RC-12, *L. acidophilus* RC-25. *L. jensenii* RC-11, *L. acidophilus* ATCC-4357, *L. plantarum* ATCC 8014, *L. fermentum* A-60 and *L. fermentum* B-54.

6. A pharmaceutical composition effective for colonizing a urogenital tract in a mammal which comprises an effective amount of at least one Lactobacillus strain selected from a group consisting of *L. casei* var. *rhamnosus* GR-1, *L. casei* var. *rhamnosus* GR-2, *L. casei* var. *rhamnosus* GR-3, *L. casei* var. *rhamnosus* GR-4, *L. casei* var. *rhamnosus* RC-17, *L. casei* NRC-430, *L. casei* ATCC-7469, *L. rhamnosus* RC-12, *L. acidophilus* RC-25, *L. jensenii* RC-11, *L. acidophilus* ATCC-4357, *L. plantarum* ATCC 8014, *L. fermentum* A-60 and *L. fermentum* B-54 wherein the lactobacillus strain is administered in unit dosage form comprising at least $10^9$ organisms.

7. A method for preventing colonization of pathogenic bacteria on epithelial surfaces of a urogenital tract in a mammal which comprises administering a therapeutically effective amount of at least one Lactobacillus strain selected from the group consisting of *L. casei* var. *rhamnosus* GR-1. *L. casei* var. *rhamnosus* GR-2, *L. casei* var. *rhamnosus* GR-3. *L. casei* var. *rhamnosus* GR-4. *L. casei* var. *rhamnosus* RC-17. *L. casei* ATCC-7469, *L. rhamnosus* RC-12, *L. acidophilus* RC-25, *L. jensenii* RC-11, *L. acidophilus* ATCC-4357, *L. plantarum* ATCC 8014, *L. fermentum* A-60 and *L. fermentum* B-54.

8. A pharmaceutical composition suitable for preventing colonization of pathogenic bacteria to epithelial cells of a urogenital tract in a mammal which comprises an effective amount of at least one Lactobacillus strain selected from the group consisting of *L. casei* var. *rhamnosus* GR-1, *L. casei* var. *rhamnosus* GR-2, *L. casei* var. *rhamnosus* GR-3, *L. casei* var. *rhamnosus* GR-4, *L. casei* var. *rhamnosus* RC-17, *L. casei* NRC-430, *L. casei* ATCC-7469, *L. rhamnosus* RC-12, *L. acidophilus* RC-25, *L. jensenii* RC-11, *L. acidophilus* ATCC-4357, *L. plantarum* ATCC 8014, *L. fermentum* A-60 and *L. fermentum* B-54 wherein the lactobacillus strain is administered in unit dosage form comprising at least $10^9$ organisms.

9. A method for forming or maintaining an indigenous protective flora adherent to uroepithelial or vaginal epithelial cells and associated mucous comprising the administration to a female mammal in need thereof of a safe and effective amount of at least one Lactobacillus strain selected from the group consisting of *L. casei* var. *rhamnosus* GR-1, *L. casei* var. *rhamnosus* GR-2, *L. casei* var. *rhamnosus* GR-3, *L. casei* var. *rhamnosus* GR-4, *L. casei* var. *rhamnosus* RC-17, *L. casei* ATCC-7469, *L. rhamnosus* RC-12, *L. acidophilus* RC-25, *L. jensenii* RC-11, *L. acidophilus* ATCC-4357, *L. plantarum* ATCC 8014, *L. fermentum* A-60 and *L. fermentum* B-54 effective to colonize said epithelial cells, and competitively exclude or minimize the presence of pathogenic bacteria in or about said epithelial cells.

10. The pharmaceutical composition of any one of claim 2, 6, or 8 wherein the unit dosage form comprises a pharmaceutically acceptable carrier.

11. The method of claim 10 wherein the pharmaceutically acceptable carrier is an encapsulating substance.

* * * * *